United States Patent [19]
Vollmueller et al.

[11] Patent Number: 5,912,392
[45] Date of Patent: Jun. 15, 1999

[54] PROCESS FOR THE PREPARATION OF 2H-HEPTAFLUOROPROPANE

[75] Inventors: Helmut Vollmueller, Mainz; Raimund Franz, Kelkheim; Guenter Siegemund, Hofheim, all of Germany

[73] Assignee: Solvay (Société Anonyme), Brussels, Belgium

[21] Appl. No.: 08/842,119

[22] Filed: Apr. 28, 1997

[30] Foreign Application Priority Data

Apr. 29, 1996 [DE] Germany .............................. 196 17 091

[51] Int. Cl.⁶ ..................................................... C07C 17/08
[52] U.S. Cl. ............................................ 570/165; 570/164
[58] Field of Search ..................................... 570/164, 165

[56] References Cited

U.S. PATENT DOCUMENTS 5,399,795  3/1995  Franz et al. .

FOREIGN PATENT DOCUMENTS

| | | |
|---|---|---|
| 2127732 | 1/1995 | Canada . |
| 0634383 | 1/1995 | European Pat. Off. . |
| 0634384 | 1/1995 | European Pat. Off. . |
| 19534917 | 4/1997 | Germany . |
| 902590 | 8/1962 | United Kingdom . |
| 97/11042 | 3/1997 | WIPO . |

*Primary Examiner*—Alan Siegel
*Attorney, Agent, or Firm*—Venable; John W. Schneller

[57] ABSTRACT

Process for the preparation of 2H-heptafluoropropane from hexafluoropropene and hydrogen fluoride in an apparatus equipped with bubble columns fitted with flow resistances, in which a liquid hydrofluoride of an organic base circulates.

10 Claims, 1 Drawing Sheet

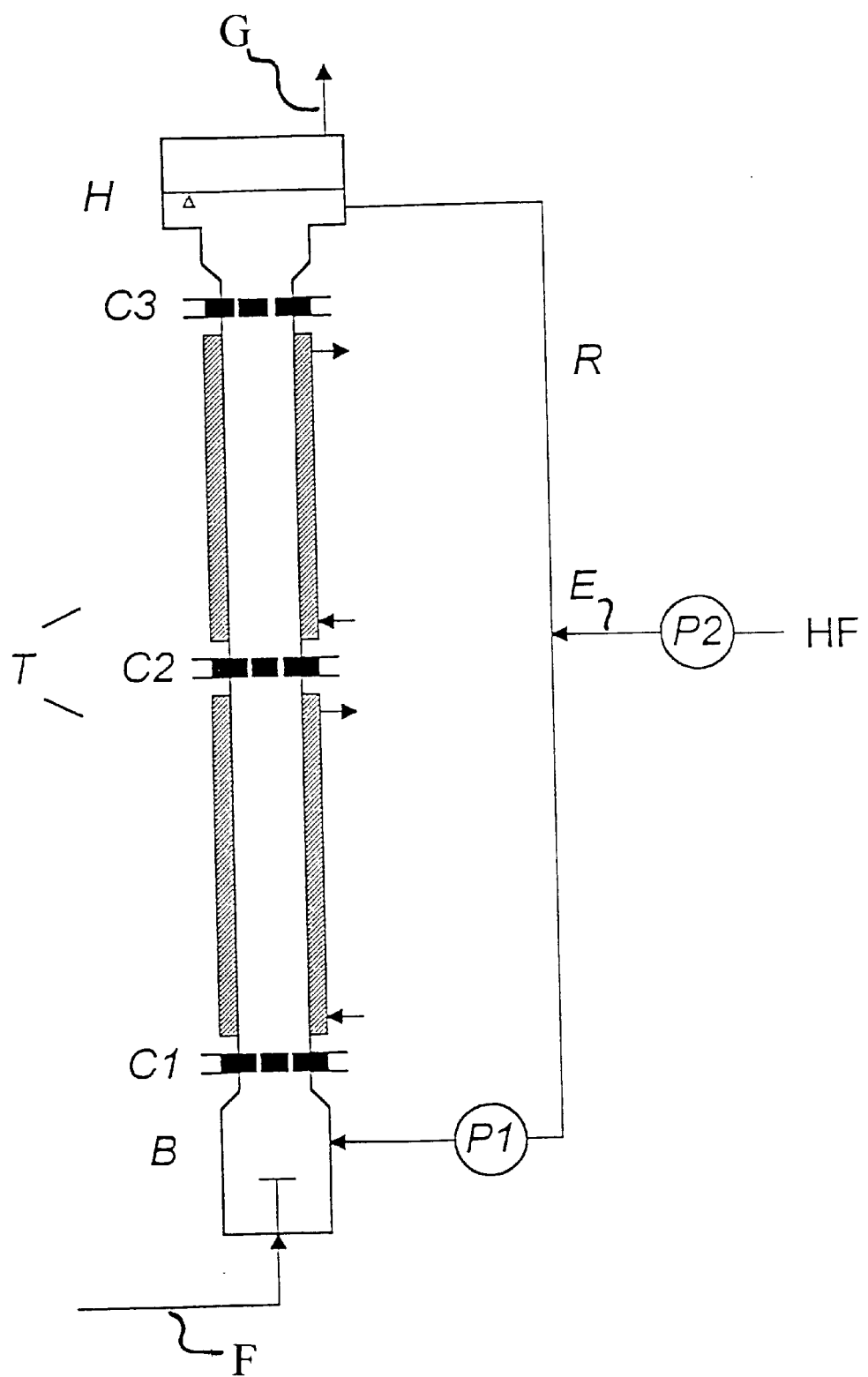

PROCESS FOR THE PREPARATION OF 2H-HEPTAFLUOROPROPANE

FIELD OF THE INVENTION

The invention relates to a process for the preparation of 2H-heptafluoropropane from hexafluoropropene in a bubble column.

Technology Review

2H-Heptafluoropropane (R 227) is a valuable technical-scale propellant and coolant, which is free of chlorine and is consequently harmless to the stratospheric ozone layer. It is advantageously prepared, with reference to the structural formula (I), by addition of hydrogen fluoride to hexafluoropropene.

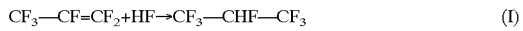

$$CF_3—CF=CF_2+HF\rightarrow CF_3—CHF—CF_3 \quad (I)$$

By way of example, it is known from document GB-902,590 to carry out this reaction at a temperature of 250 to 450° C. over an active charcoal catalyst. In contrast with the process of this type catalysed on a fixed bed, document EP-A-0,634,383 proposes to introduce gaseous hexafluoropropene into a reactor fitted with bubble columns only at a temperature of 20 to 80° C., the reactor containing, as reaction medium and as catalyst, a liquid hydrofluoride complex of an organonitrogen base corresponding to the general formula

$$[B \cdot nHF] \quad (II)$$

where n represents an integer or a fraction <4 and B represents an organonitrogen base.

In this way, a molecule of HF orginating from the hydrofluoride adds to a molecule of hexafluoropropene, such that at the surface of the liquid, the gaseous 2H-heptafluoropropane escapes in the form of reaction product. The reaction medium is guided into a closed circuit via an external tubular pipe and is regenerated under these circumstances by continuous addition of hydrogen fluoride.

Usually, a fine dispersion of a gas guided into a bubble column is obtained, which is required for rapid and complete reaction, for example using a sinter consisting of a sintered material, or alternatively via a stirrer. However, during the hydrofluorination of hexafluoropropene into heptafluoropropane in the liquid complex (II), difficulties arise which are associated with the degree of solubility of the two gases in this reaction medium. Under typical reaction conditions, the hexafluoropropene is soluble to an amount of 44 g/(kg.bar) and the heptafluoropropane itself up to an amount of 63 g/(kg.bar). Consequently, an intense dispersion may have the consequence of fully dissolving the gases and causing the bubbles to disappear. However, this gives rise to supersaturation of the reaction medium with heptafluoropropane, which only escapes from the liquid in a non-uniform manner and in bursts, it being possible for this supersaturation to lead to excessive formation of foam. In addition, it may occur that gas is released in undesirable places, for example in the pump for circulating the reaction medium. In this case, the output capacity of the pump decreases. It is true that supersaturation and the consequences thereof may be prevented by increasing the flow rate of the gas, which increases the number of gas bubbles, or alternatively by decreasing the degree of dispersion, such that larger bubbles are obtained; however, these measures usually lead to a decrease in the conversion, as demonstrated below in a comparative example. Consequently, the objective consisting in maintaining the concentration of unreacted hexafluoropropene in the gaseous reaction products at a value below 100 ppm can be achieved only under very rigorously defined and delimited conditions.

Unpublished German patent application P 195 34 917.2-4 proposed, when carrying out this process, to raise the pressure in the reactor to a value of 1.3 to 10 bar using a flow control valve in order thereby to maintain the two gases fully in solution. Thus, complete conversion of the hexafluoropropene is obtained; in addition, the heptafluoropropane is released in a reliable manner during the depressurization of the reaction medium circulating behind the flow control valve.

However, under such reaction conditions, the hexafluoropropene is able to react not only with HF but also with itself to form hexafluoropropene di-and trimeric homologues. This tendency towards self-addition depends on the concentration and is consequently promoted by a higher pressure. It is true that the self-addition is still very minimal up to an excess pressure of 0.7 bar (measured at the bottom of the reactor); however, above this value, it increases appreciably and, in the process according to document P 195 34917.2-4, it is acceptable only in a narrow excess pressure range which must be monitored constantly. At the same time, a clear upper limit is likewise imposed on the flow rate of the gas, given that above this limit, at constant pressure, bubbles would again be obtained, although, in this process, the reaction medium must remain free of bubbles. The hexafluoropropene di-and trimers obtained at higher pressures do not react by addition with HF originating from the reaction medium. Given that they are partially toxic, the heptafluoropropane must be separated therefrom via a careful and expensive fractional distillation.

SUMMARY OF THE INVENTION

Consequently, the object was to find a process using bubble columns for the preparation of heptafluoropropane from hexafluoropropene and HF, in which the abovementioned problems do not occur, in which process a quantitative conversion of the hexafluoropropene and a reliable release of pure heptafluoropropane are obtained, also in the absence of complete dissolution of the gases which is forced via a flow control valve under elevated pressure.

This object is achieved in accordance with the invention by using a specially-quipped bubble column. The subject of the invention consequently relates to a process for the preparation of 2H-heptafluoropropane from hexafluoropropene and hydrogen fluoride in an apparatus equipped with bubble columns filled with, as reaction medium, a liquid hydrofluoride of an organonitrogen base corresponding to the general formula

$$[B \cdot nHF] \quad (II)$$

where B represents an organonitrogen base and n represents an integer or a fraction <4, preferably >2 and <3, characterized in that a bubble column fitted with a system for recycling the reaction medium is used, comprising a base part (P), a reaction tube (T) and a head part (H), process wherein a high degree of dispersion of the gases is maintained in the reaction medium in the reaction tube (T), but a complete dissolution of said gases in said reaction medium is avoided. Such conditions are obtained for example by using a reaction tube (T) which is equipped with at least one flow resistance giving rise to an acceleration of the flow of the liquid reaction medium by a factor of at least 20 as it passes through this resistance.

DETAILED DESCRIPTION OF THE INVENTION

Generally, a flow resistance which gives rise to an acceleration of the flow of the liquid medium not exceeding 200 is used. Flow resistances leading to an acceleration of the flow of from 50 to 100 are preferred.

Any device which allows the reaction medium to be accelerated in the above proportions may be used as flow resistance. A plate placed in the reaction tube (T) so as to occupy its entire cross-section and pierced with small holes, referred to hereinbelow as bores, is advantageously used. Generally, this plate is placed transversely in the reaction tube (T) and the bores are placed along the axis of the reaction tube (T). They thus preferably extend in an axial direction relative to the reaction tube (T). The bores preferably consist of cylindrical holes having lengths which are at least equal and at most twice their diameter. A ratio of the length to the diameter of about 2 is preferred. By way of example, bores having a diameter of from 0.1 to 1 cm may be used. The number of bores required is calculated such that the flow of the liquid reaction medium (without taking the gas bubbles into account) is accelerated by at least a factor of 20 as it passes through the bores. To do this, the ratio of the total cross-sectional area of the bores of a flow resistance to the cross-sectional area of the reaction tube (T) needs to be not more than 0.05.

The reaction tube (T) is preferably equipped with at least two flow resistances, one being close to the base part (P) and the other close to the head part (H) of the bubble column. When the length of the reaction tube (T) exceeds 2 m, one or more intermediate flow resistances are also preferably fitted.

For the purposes of the present invention, the flow rate of the reaction medium is expressed on the liquid basis, that is to say without taking account of the volume occupied by the gas bubbles. Usually, the reaction medium is circulated in the bubble column at a flow rate in the reaction tube (T) ($V_T$) of from 1 to 20 cm/s. Preferably, this flow rate is from 2 to 10 cm/s. In a particularly preferred manner, it is from 3 to 7 cm/s. On the other hand, the flow rate of the reaction medium as it passes through each flow resistance ($V_C$) represents from 20 to 200 times the value $V_T$. Preferably, $V_C$ is at least 200 cm/s.

By maintaining a flow rate $V_T$ of at least 1 cm/s and a $V_C$ rate of at least 200 cm/s, the process according to the invention exhibits three characteristics:

1) a large number of very finely divided gas bubbles is always obtained at each flow resistance,
2) the formation of gas bubbles at the flow resistances is independent of the solubility and the degree of dissolution of the gases in the reaction medium,
3) the heptafluoropropane is completely released from the liquid in gas form at the highest-placed flow resistance.

The height of the level of liquid to be maintained in the bubble column used in the process according to the invention is delimited, on the one hand, by the minimum residence time required for the substrate in the reaction medium, and, on the other hand, by the hydrostatic pressure being exerted on the base of the column. It is preferably from 2.5 to 4 m, in particular 3 to 3.5 m. The level of the reaction liquid is generally at 20–80 cm, preferably 20–40 cm, above the highest-placed flow resistance.

Advantageously, a high flow rate of hexafluoropropene is selected such that in addition to the liquid reaction medium, gas bubbles also penetrate into the flow resistances. Thus, the capacity of the apparatus is increased greatly compared with that described in document P 195 34 917.2-4: the flow rate range which can be used in practice, with a given inside diameter of the reactor, is in this case only limited by the minimum residence time required for the substrate in the reaction medium, that is to say by the height of the reactor. The maximum excess pressure of liquid which intervenes in the base part P of the reactor may be maintained at a value below 0.7 bar by adjusting a suitable capacity of the circulation pump and is consequently always less than that prevailing in the apparatus according to document P 195 34 917.2-4.

The formation of di-and trimeric hexafluoropropene homologues remains very minimal.

The maximum possible flow rate of the hexafluoropropene depends on the cross-sectional area of the reaction tube (T) of the bubble column. It may be 100 g per hour and per $cm^2$ of cross-section of the reaction tube (T). In practice, a flow rate of from 40 to 80 g/($cm^2$.h) is preferred.

In a preferred embodiment of the process according to the invention, a bubble column is used fitted with a reaction tube (T) having a length of 200 to 350 cm, preferably from 250 to 300 cm, and an inside diameter of 3 to 50 cm, preferably from 5 to 20 cm, equipped, at its lower end, at mid-height and at its upper end, with three flow resistances. Preferably, the middle flow resistance is found, when the distance between the end flow resistances is divided into 100 equal parts, between the 35-point section and the 65-point section.

An apparatus suitable for this preferred embodiment is described below and is represented diagramatically in FIG. 1.

The bubble column consists of a base part B, a reaction tube T which consists of parts which may be externally heated with hot water, and of a head part H. At the lower end, at mid-height and at the upper end of the reaction tube T are applied in total three flow resistances C1, C2 and C3 which each have bores. The level of the reaction liquid is denoted by D. The tubular pipe R and the pump P1 serve to recycle the liquid contents of the reactor such that they pass through the bores of the flow resistances in a constantly ascending manner. The supply pipe E serves to introduce, continuously in a dosed manner, liquid hydrogen fluoride into the tube R by means of the pump P2. An HF-resistant material is needed for the supply pipe E and for its environment. For all the other parts of the apparatus, besides steel or polyolefin synthetic materials, borosilicate glass may also be used. The supply pipe F serves to introduce continously hexafluoropropene, preferably in the gaseous state. In order to control the supply of hexafluoropropene and of HF, corresponding devices for weighing and measuring the flow rate are provided. The pipe G serves to withdraw gaseous heptafluoropropane.

As has already been mentioned in the introduction, the hydroflurination of hexafluoropropene takes place in accordance with document EP-A-0,634,383 in the reaction temperature range from 20 to 80° C. On the basis of the viscosity of the reaction medium, a range from 60 to 75° C. is preferred.

Suitable hydrofluorides, which are liquid at these temperatures, corresponding to Formula (II) are, for example, $[(CH_3)_3N \times nHF]$, $[(C_2H_5)_3N \times nHF]$, $[(C_4H_9)_3N \times nHF]$, as well as

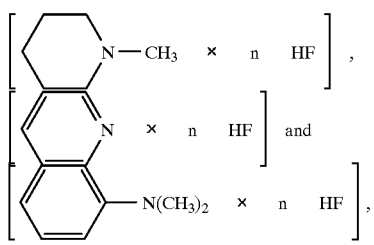

with 2<n<3.

Preferably, one of the first three hydrofluorides mentioned is used. However, all the other hydrofluorides corresponding to Formula (II), mentioned in document EP-A-0,634,383, which are liquid at the reaction temperatures chosen, are also suitable. The preparation of the hydrofluorides is also described in document EP-A-0,634,383, to which reference is made explicitly herein. Besides hexafluoropropene, the halogenated alkenes indicated in that document may be converted in a manner similar to that of the present process, during which process they react in a yield which is about as high as that of the hexafluoropropene.

EXAMPLES

The exemplary embodiments below explain the process according to the invention.

Example 1

In accordance with FIG. 1, a borosilicate glass apparatus equipped with a bubble column is mounted, in which the reaction tube T consists of two parts fitted with a jacket and which may be heated, having a length of 120 cm and an inside diameter of 5 cm respectively, and the flow resistances C1, C2 and C3 are polypropylene plates 0.5 cm in thickness and respectively having four axial bores 0.3 cm in diameter. The recycling tube R and the pipe E for supplying HF are made of stainless steel. This apparatus is filled to a height of about 25 cm above the flow resistance C3 with the liquid catalyst $[(n-C_4H_9)_3N \cdot 2.2HF]$, which is then heated to 75° C. with hot water and is circulated in a closed circuit at a flow rate of 380 l/h with the aid of a circulation pump P1. The flow rate of the catalyst in the reaction tube T is consequently 5.4 cm/s and the flow rate inside the flow resistance bores is 368 cm/s.

Hexafluoropropene is then introduced from a pressurized reservoir bottle, at a flow rate of 500 g/h (corresponding to 25 g/(cm².h)) in gaseous form into the bottom of the column. The large gas bubbles which form at the site of the introduction device are finely divided as they pass through the flow resistance C1 and are subjected to virtually complete decomposition during the continuation of their movement to the flow resistance C2. At the flow resistance C2, a large amount of finely divided gas bubbles is again obtained which, nevertheless, after they have moved about a further 50 cm towards the flow resistance C3, undergo complete decomposition. The gas bubbles again finely divided, which form at the flow resistance C3, rapidly end up at the liquid surface in the head part H of the bubble column. At this location, the gas is freed in the form of a steady stream, it is guided via a tubular pipe into a trap cooled with carbon dioxide snow and it condenses therein. The yield is quantitative, given that, even after running for several hours, no increase in the volume of the liquid catalyst is observed and no evolution of gas in the recirculation pump takes place. The hydrogen fluoride consumed in the course of the conversion is replaced continuously using a membrane pump P2 from a stainless steel reserve container, via the supply pipe E.

The product collected in the cooling trap is subjected to analysis by gas chromatography and identified as being virtually pure 2H-heptafluoropropane. Thereafter, eluted components of higher boiling point are found in a total concentration of 314 ppm. No hexafluoropropene is detected.

Example 2

In this experiment, which is otherwise carried out as described in Example 1, the hexafluoropropene is introduced at a flow rate virtually twice as fast, of 970 g/h (corresponding to 49 g/(cm².h)). In the reaction tube, between the flow resistances C2 and C3, in contrast with the experiment of Example 1, complete dissolution of the gas is not observed, but a uniform distribution of larger bubbles. The yield is quantitative and components of higher boiling point are obtained, in an amount of 457 ppm. No hexafluoropropene is detected.

Example 3

In an experiment which is otherwise carried out as described in Example 1, the hexafluoropropene is introduced at a flow rate of 1800 g/h (corresponding to 92 g/(cm².h)). The total reaction tube T remains densely filled with finely divided gas bubbles throughout this experiment. The yield is again quantitative; components of higher boiling point are found, in a concentration of 361 ppm, as well as unreacted hexafluoropropene in an amount of 53 ppm.

Example 4

In an experiment which is otherwise carried out as described in Example 2, the temperature of the circulating liquid catalyst is only 66° C. However, the result is practically the same: the gas produced is also released in quantitative form; components of higher boiling point are found, in an amount of 334 ppm, and no hexafluoropropene is detected in the gas chromatogram.

Comparative Example

A paddle stirrer of adjustable speed of rotation is mounted into the base part P apparatus equipped with bubble columns, as described in Example 1, for dispersion of the gas, but without, however, the flow resistances denoted by C1–C3 in FIG. 1. The temperature in the reaction medium is still at 75–79° C. The concentration, determined by gas chromatography, of the unreacted hexafluoropropene in the produced as a function of three different adjustable reaction parameters is represented in Table 1.

TABLE 1

| Flow rate of recycling (l/h) | Flow rate of the hexafluoro-propene (g/h) | Speed of rotation of the stirrer (min⁻¹) | Hexafluoro-propene in the gas pro-duced (ppm) | Comments |
|---|---|---|---|---|
| 500 | 200 | 4000 | — | |
| 500 | 200 | 3000 | — | a) |
| 500 | 200 | 2000 | 133 | |
| 500 | 200 | 1500 | 919 | b) |
| 500 | 400 | 3000 | 92 | |
| 1000 | 400 | 3000 | 314 | c) |
| 500 | 840 | 3000 | 2182 | d) |

TABLE 1-continued

| Flow rate of recycling (l/h) | Flow rate of the hexafluoro-propene (g/h) | Speed of rotation of the stirrer (min⁻¹) | Hexafluoro-propene in the gas produced (ppm) | Comments |
|---|---|---|---|---|
| 500 | 880 | 4000 | 461 | |
| 500 | 840 | 5000 | 125 | |
| 1000 | 200 | 3000 | 0 | |
| 500 | 400 | 4000 | 12 | |

The comments relating to the individual implementations of the comparative are as follows:

a) No measurement of the hexafluoropropene concentrations in the gas produced can be made, given that the reaction mixture is supersaturated with hexafluoropropene.

b) On account of the minimal rotation speed, the distribution of the gas in the reaction solution is too poor to be able to obtain a complete conversion.

c) On account of the high recycling flow rate, the residence time is too short in this case to obtain a complete conversion.

d) In this case, the flow rate for a complete conversion is too high. In general, the process is performed at rotation speeds below 4000 min⁻¹, given that higher rotation speeds consume a lot of energy.

What is claimed is:

1. A process for the preparation of 2H-heptafluoropropane from hexafluoropropene and hydrogen fluoride in an apparatus equipped with at least one bubble column filled with, as reaction medium, a liquid hydrofluoride of an organonitrogen base corresponding to the general formula

[B·nHF]            (II)

where B represents an organonitrogen base and n represents an integer or a fraction ≦4, said bubble column fitted with a system for recycling reaction medium used, comprising a base part (P), a reaction tube (T) equipped with at least one flow resistance giving rise to an acceleration of the liquid reaction medium flow as it passes through said resistance and a head part (H), said process in said apparatus including maintaining a high degree of dispersion of the gases in the reaction medium in the reaction tube (T), but avoiding a complete dissolution of said gases in said reaction medium.

2. The process in said apparatus according to claim 1, wherein said is at least one flow resistance gives rise to an acceleration of the flow of the liquid reaction medium by a factor of at least 20.

3. The process in said apparatus according to claim 2, in which the flow resistance gives rise to an acceleration of the flow of the liquid medium by a factor of 50 to 100.

4. The process in said apparatus according to claim 2, in which a plate placed transversely in the reaction tube (T) and pierced with bores arranged along the axis of the reaction tube (T) is used as flow resistance.

5. The process in said apparatus according to claim 4, in which the bores consist of cylindrical holes having lengths which are at least equal and at most twice their diameter.

6. The process in said apparatus according to claim 1, in which the reaction tube (T) is equipped with at least two flow resistances.

7. The process in said apparatus according to claim 1, in which the reaction medium is circulated in the reaction tube (T) at a flow rate of from 1 to 20 cm/s.

8. The process in said apparatus according to claim 2, in which the flow rate of the reaction medium as it passes through a flow resistance is at least 200 cm/s.

9. The process in said apparatus according to claim 1, in which the height of the level of liquid in the bubble column is between 2.5 and 4 m.

10. The process according to claim 1, in which an excess pressure below 0.7 bar is maintained in the base part (P) of the reactor.

* * * * *